(12) United States Patent
Wheatley (10) Patent No.: US 11,357,544 B2
(45) Date of Patent: Jun. 14, 2022

(54) SYSTEMS AND METHODS FOR INTRODUCING A STIMULATION LEAD INTO A PATIENT

(71) Applicant: Boston Scientific Neuromodulation Corporation, Valencia, CA (US)

(72) Inventor: Rhys Wheatley, Sonoma, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 785 days.

(21) Appl. No.: 16/254,209

(22) Filed: Jan. 22, 2019

(65) Prior Publication Data

US 2019/0223910 A1    Jul. 25, 2019

Related U.S. Application Data

(60) Provisional application No. 62/621,837, filed on Jan. 25, 2018.

(51) Int. Cl.
| | |
|---|---|
| *A61B 17/34* | (2006.01) |
| *A61N 1/05* | (2006.01) |
| *A61N 1/372* | (2006.01) |
| *A61B 17/32* | (2006.01) |

(52) U.S. Cl.
CPC ........ *A61B 17/3468* (2013.01); *A61N 1/0553* (2013.01); *A61N 1/372* (2013.01); *A61B 2017/320056* (2013.01); *A61N 1/0551* (2013.01)

(58) Field of Classification Search
CPC .... A61B 17/3468; A61B 2017/320056; A61N 1/0053; A61N 1/372; A61N 1/0551
See application file for complete search history.

(56) References Cited

U.S. PATENT DOCUMENTS

| | | |
|---|---|---|
| 4,285,347 A | 8/1981 | Hess |
| 5,193,539 A | 3/1993 | Schulman et al. |
| 5,193,540 A | 3/1993 | Schulman et al. |
| 5,312,439 A | 5/1994 | Loeb |
| 5,324,316 A | 6/1994 | Schulman et al. |
| 5,405,367 A | 4/1995 | Schulman et al. |
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |

(Continued)

*Primary Examiner* — Anh T Dang
(74) *Attorney, Agent, or Firm* — Branch Partners PLLC; Bruce E. Black (57) ABSTRACT

A lead-implantation tool for implanting a lead into a patient includes an elongated body having a distal portion with a tip configured to separate patient tissue to form, or extend through, a tunnel in the tissue when the body is advanced along the tissue. A lead-retention element is formed along the distal portion of the body and includes a cutout defined along the body with a cutout surface wall inset from the body's outer surface. A protrusion extends outwardly from the cutout surface wall with at least a portion of the protrusion extending towards the tip. The protrusion is entirely inset from, or flush with, the body's outer surface. The protrusion is configured to removably receive and retain a portion of the lead while the distal portion of the body is advanced along the tissue and to separate from the lead as the body is withdrawn from the tissue.

20 Claims, 6 Drawing Sheets

(56) References Cited

U.S. PATENT DOCUMENTS

| | | |
|---|---|---|
| 7,392,093 B2 | 6/2008 | Khan |
| 7,450,997 B1 | 11/2008 | Pianca et al. |
| 7,519,433 B2 | 4/2009 | Foley |
| 7,660,631 B2 | 2/2010 | Whitehurst et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,175,710 B2 | 5/2012 | He |
| 8,214,048 B1 | 7/2012 | Whitehurst et al. |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,688,235 B1 | 4/2014 | Pianca et al. |
| 9,283,394 B2 | 3/2016 | Whitehurst et al. |
| 2002/0143376 A1 | 10/2002 | Chinn et al. |
| 2006/0036286 A1 | 2/2006 | Whitehurst et al. |
| 2007/0150036 A1 | 6/2007 | Anderson |
| 2009/0187222 A1 | 7/2009 | Barker |
| 2009/0276021 A1 | 11/2009 | Meadows et al. |
| 2010/0030227 A1* | 2/2010 | Kast .................. A61B 17/3468 606/129 |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0071540 A1 | 3/2011 | Kast et al. |
| 2011/0078900 A1 | 4/2011 | Pianca et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGlore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0197602 A1 | 8/2013 | Pianca et al. |
| 2015/0133954 A1* | 5/2015 | Seifert .............. A61B 17/3468 606/129 |
| 2015/0258813 A1 | 9/2015 | Seaver et al. |
| 2015/0343197 A1 | 12/2015 | Gardeski et al. |
| 2016/0166828 A1 | 6/2016 | Yu |
| 2019/0060643 A1 | 2/2019 | Leven et al. |

\* cited by examiner

SYSTEMS AND METHODS FOR INTRODUCING A STIMULATION LEAD INTO A PATIENT

CROSS-REFERENCE TO RELATED APPLICATIONS

This application claims the benefit under 35 U.S.C. § 119(e) of U.S. Provisional Patent Application Ser. No. 62/621,837, filed Jan. 25, 2018, which is incorporated herein by reference.

FIELD

The present invention is directed to the area of implantable stimulation systems and methods of making and using the systems and, in particular, to a lead implantation tool for facilitating implantation of a stimulation lead into a patient, as well as methods of making and using the lead implantation tool.

BACKGROUND

Implantable stimulation systems, such as electrical stimulation systems, have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

In one aspect, a lead implantation tool for facilitating implantation of a stimulation lead into a patient includes a body and a lead-retention element. The body has an elongated shape with an outer surface, a longitudinal length, a diameter, a proximal portion, and a distal portion with a blunt tip configured to separate patient tissue to form, or extend through, a tunnel in the patient tissue when the body is advanced along the patient tissue. The lead-retention element is formed along the distal portion of the body and includes a cutout and a protrusion. The cutout is defined along a side of the body and includes a cutout surface wall inset from the outer surface of the body. The protrusion extends outwardly from the cutout surface wall with at least a portion of the protrusion extending towards the blunt tip. The protrusion is entirely inset from, or flush with, the outer surface of the body. The protrusion is configured to removably receive and retain a portion of the stimulation lead while the distal portion of the body is advanced along patient tissue and to separate from the stimulation lead as the distal portion of the body is withdrawn from the tunnel in the patient tissue.

In at least some embodiments, one or more tissue separation members extend radially outward from the outer surface of the distal portion of the body and are configured to separate patient tissue to expand the tunnel along at least one lateral dimension when the body is advanced along patient tissue. In at least some embodiments, each of the one or more tissue separation members includes a multi-peak structure with a first peak and at least one second peak that is longitudinally-offset from and radially-aligned with the first peak along the body of the lead implantation tool. In at least some embodiments, the first peak is positioned distally to the at least one second peak along the body of the lead implantation tool and extends radially outward from the outer surface of the body by an amount that is less than each of the at least one second blades.

In at least some embodiments, the protrusion is proximal to each of the one or more tissue separation members along the longitudinal length of the body. In at least some embodiments, the lead implantation tool includes two of the tissue separation members which are circumferentially offset from one another along the body by 180 degrees. In at least some embodiments, the protrusion is circumferentially offset from each of the two tissue separation members along the body by at least 70 degrees and no more than 110 degrees. In at least some embodiments, a distal-most portion of the protrusion is longitudinally-offset from the blunt tip by no more than 2 cm. In at least some embodiments, the protrusion extends parallel to the longitudinal length of the body.

In at least some embodiments, the body is flexible. In at least some embodiments, the lead implantation tool further includes a handle disposed along the proximal portion of the body.

In other aspects, a medical device kit includes any of the above-mentioned lead implantation tools and a stimulation lead. The stimulation lead includes a lead body having an elongated shape with a proximal portion and a distal portion, and a tool-receiving element is configured to removably couple with the lead-retention element of the lead implantation tool so that, when the tool-receiving element is coupled with the lead-retention element, movement of the lead implantation tool causes a corresponding movement of the distal portion of the lead body of the stimulation lead. In at least some embodiments, the tool-receiving element is formed as one of an aperture, an eyelet, or a loop of material.

In at least some embodiments, the stimulation lead is an electrical stimulation lead, the electrical stimulation lead including at least one terminal disposed along the proximal portion of the lead body and at least one electrode coupled to the at least one terminal. In at least some embodiments, the electrical stimulation lead is a paddle lead with a paddle body disposed along the distal portion of the lead body, and where the at least one electrode is disposed along a paddle body. In at least some embodiments, the tool-receiving element is disposed along the paddle body.

In yet other aspects, a method for implanting a stimulation lead into a patient includes providing any of the above-mentioned lead implantation tools. The lead-retention element of the lead implantation tool is coupled to a distal portion of the stimulation lead. The lead implantation tool is advanced along a tunnel formed along patient tissue with the distal portion of the stimulation lead coupled to the lead-retention element. The lead-retention element is separated from the stimulation lead. The lead implantation tool is removed from the tunnel leaving the stimulation lead disposed in patient tissue.

In at least some embodiments, separating the lead-retention element from the stimulation lead includes withdrawing the lead implantation tool along the tunnel, the withdrawal causing the stimulation lead to separate from the protrusion of the lead-retention element.

In still yet other aspects, a method for implanting a stimulation lead into a patient includes providing any of the above-mentioned lead implantation tools. A tunnel is formed in patient tissue using the lead implantation tool. The lead-retention element of the lead implantation tool is coupled to a distal portion of the stimulation lead. The lead implantation tool is advanced through the tunnel with the distal portion of the stimulation lead coupled to the lead-retention element. The lead-retention element is separated from the stimulation lead. The lead implantation tool is removed from the tunnel leaving the stimulation lead within the patient. In at least some aspects, forming a tunnel in patient tissue using the lead implantation tool includes forming a tunnel configured to receive a paddle body of the stimulation lead.

In other aspects, a method for implanting a stimulation lead into a patient includes providing any of the above-mentioned lead implantation tools. The lead-retention element of the lead implantation tool is coupled to a distal portion of the stimulation lead. The lead implantation tool is advanced along patient tissue with the distal portion of the stimulation lead coupled to the lead-retention element. The lead-retention element is separated from the stimulation lead as the lead implantation tool is withdrawn from the patient tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable stimulation systems and methods of making and using the systems and, in particular, to a lead implantation tool for facilitating implantation of a stimulation lead into a patient, as well as methods of making and using the lead implantation tool.

Suitable implantable stimulation systems include, for example, electrical stimulation systems, optical stimulation systems, or the like or combinations thereof. Electrical stimulation systems, include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Suitable implantable electrical stimulation systems may also include one or more microstimulators, which include an implantable control module containing electrical circuitry connected to one or more electrodes that extend through, or along, one or more walls of the control module. In some instances, microstimulators include segmented electrodes. Examples of microstimulators are found in, for example, U.S. Pat. Nos. 5,193,539; 5,193,540; 5,312,439; 5,324,316; 5,405,367; 7,660,631; 8,214,048; 9,283,394; and U.S. Patent Applications Publication No. 2006/0036286, all of which are incorporated by reference.

Figure 1:
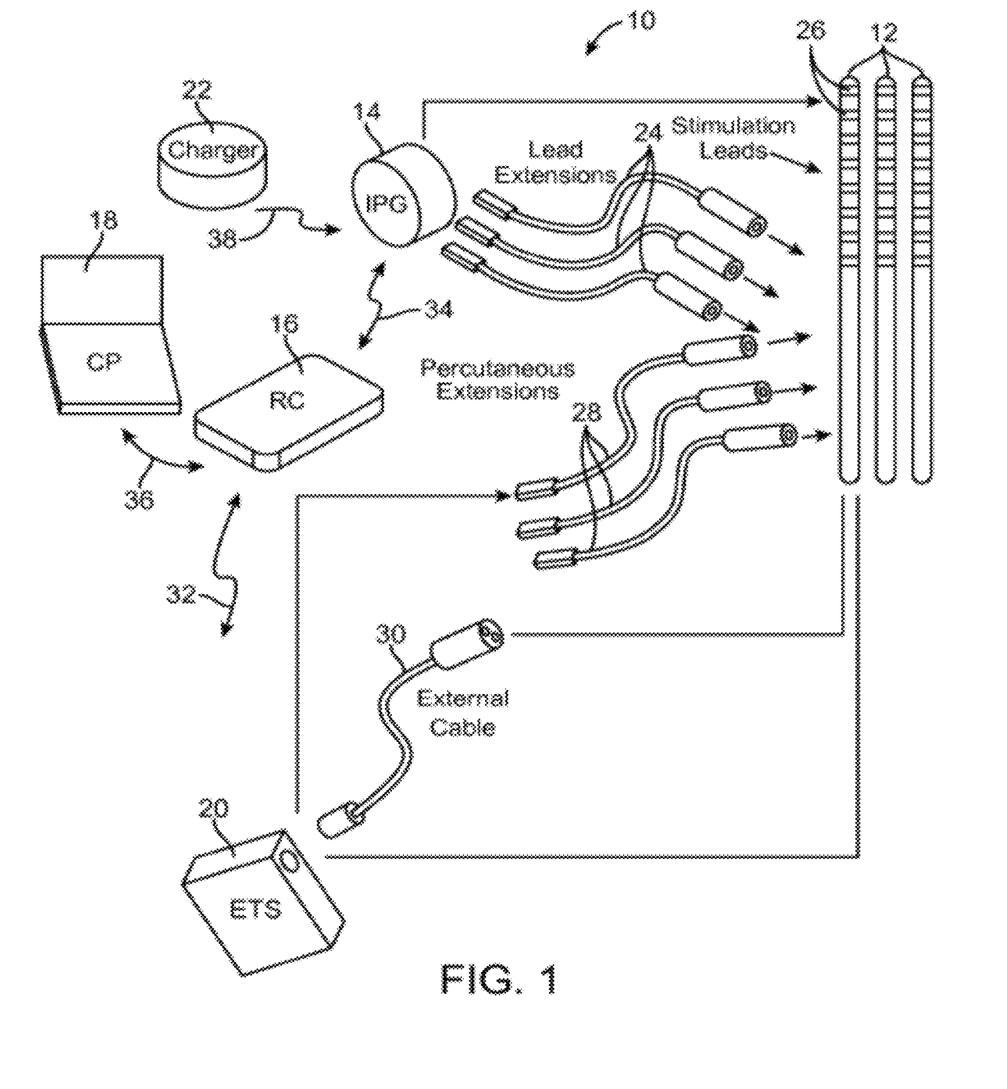
FIG. 1 is a schematic view of one embodiment of an electrical stimulation system, according to the invention.

Turning to FIG. 1, in the discussion below a percutaneous lead will be exemplified, but it will be understood that the methods and systems described herein are also applicable to paddle leads and other leads, as well as to microstimulators. Additionally, the leads are described herein relative to use for occipital nerve and/or orbital nerve stimulation, but it will be understood that any of the leads can be used for applications other than occipital nerve and/or orbital nerve stimulation, including, spinal cord stimulation, peripheral nerve stimulation, dorsal root ganglion stimulation, sacral nerve stimulation, or stimulation of other nerves, muscles, and tissues.

One embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programmed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figures 2A, 2B:
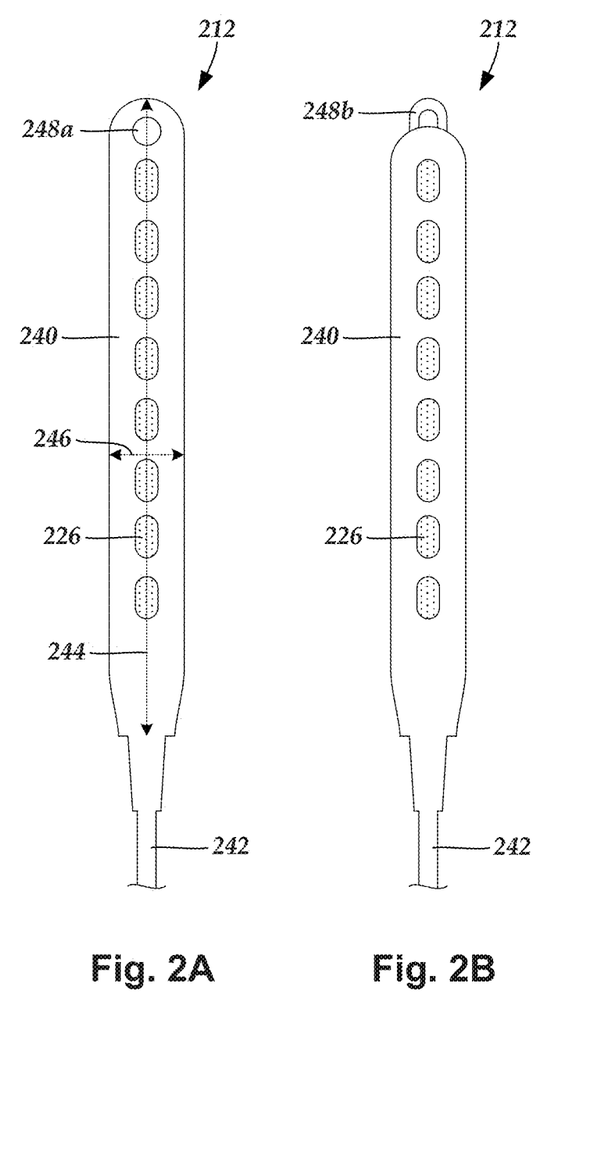
FIG. 2A is a schematic side view of one embodiment of a distal portion of a paddle lead of an electrical stimulation system, according to the invention.
FIG. 2B is a schematic side view of another embodiment of a distal portion of the paddle lead of FIG. 2A, according to the invention.
Figure 3:
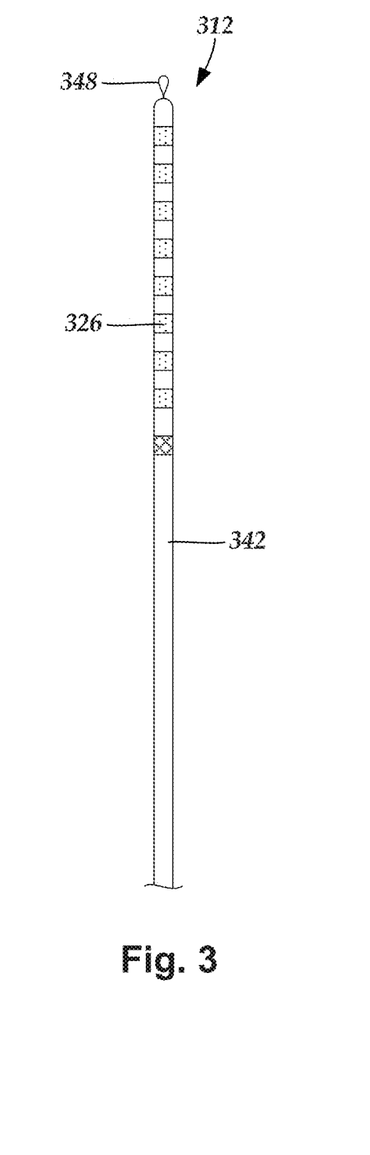
FIG. 3 is a schematic side view of one embodiment of a distal portion of a percutaneous lead of an electrical stimulation system, according to the invention.

Turning to FIGS. 2A-3, the term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension 24, an adaptor, a splitter, or the like) are disposed between the lead(s) and the control module. The leads can be formed in any suitable shape for being implanted within a patient. Some lead types include paddle leads and percutaneous leads. Other types of leads can also used, such as cuff leads.

FIG. 2A shows, in schematic side view, one embodiment of a distal portion of a paddle lead 212 of an electrical stimulation system (e.g., electrical stimulation system 10 of FIG. 1). FIG. 2B shows a second embodiment of the paddle lead 212 in schematic side view. In both embodiments, the paddle lead includes a paddle body 240 coupled to a distal portion of one or more lead bodies 242. The paddle body 240 has a longitudinal length 244 (i.e., a length dimension) and a first transverse length 246 (i.e., a width dimension) orthogonal to the longitudinal length 244. In at least some embodiments, the first transverse length 246 is larger than the diameters of each of the one or more lead bodies 242. The paddle body 240 further includes a second transverse length (i.e., a height dimension) (not shown) orthogonal to both the longitudinal length and the first transverse length.

One or more electrodes, such as electrode 226, are disposed along the paddle body and are configured for delivering electrical stimulation to patient tissue in proximity to the paddle body when the lead is implanted in the patient. In at least some embodiments, the one or more electrodes are disposed along a first major surface extending parallel to the first transverse length of the paddle body.

FIG. 3 shows, in schematic side view, one embodiment of a distal portion of a percutaneous lead 212 of an electrical stimulation system (e.g., electrical stimulation system 10 of FIG. 1). As shown in FIG. 3, one or more electrodes, such as electrode 326, are disposed along a distal portion of a lead body 342. In at least some embodiments, the distal portion of the percutaneous lead body is isodiametric proximal to a distal tip of the lead. In at least some embodiments, the portion of the percutaneous lead body along which the electrodes are disposed is isodiametric proximal to the tip of the lead.

Referring to FIGS. 2A-3 collectively, any suitable number of electrodes can be disposed along the lead including, for example, one, two, three, four, five, six, seven, eight, nine, ten, twelve, sixteen, twenty-four, thirty-two, sixty-four or more electrodes. In each of the leads shown in FIGS. 2A-3, eight electrodes are shown.

The paddle body and/or lead body can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in a patient, the lead may be in contact with body tissue for extended periods of time (e.g., no less than one day, one week, one month, one year, or more).

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use. Each of the electrodes can either be used or unused (OFF). When the electrode is used, the electrode can be used as an anode or cathode and carry anodic or cathodic current. In some instances, an electrode might be an anode for a period of time and a cathode for a period of time.

With regards to paddle leads, when the paddle lead includes multiple electrodes, the electrodes can be disposed along the paddle body in any suitable configuration. For example, in some embodiments the electrodes are arranged into one or more columns, or rows, or both. In the embodiment of the lead shown in FIGS. 2A-2B, the electrodes are arranged into a single column extending parallel to the longitudinal length of the paddle body.

In some instances, paddle bodies can be formed with different length, width, and height dimensions to accommodate implantation in many different possible locations within a patient. For example, in some embodiments the paddle body is formed with a height dimension that is small enough to be implanted along a patient's head, external to the patient's skull. In at least some embodiments, the paddle body has a height dimension is no greater than 0.05 inches (0.13 cm). In at least some embodiments, the paddle body has a height dimension is no greater than 0.04 inches (0.1 cm). In at least some embodiments, the paddle body has a height dimension is no greater than 0.03 inches (0.08 cm). In at least some embodiments, the paddle body has a height dimension is no greater than 0.02 inches (0.05 cm).

As will be described in more detail below, the distal portions of the lead 212, 312 further include one or more tool-receiving elements for facilitating implantation of the lead into a patient. The tool-receiving elements are configured for coupling with, and being retained by, a lead implantation tool while the lead implantation tool is advanced along patient tissue, and separating from the lead implantation tool while disposed in the patient. The tool-receiving element can include any element coupled to, coupleable to, or formed along the lead and suitable for removably coupling with the lead implantation tool.

In at least some embodiments, the tool-receiving elements are configured to removably receive a protrusion extending from a portion of the lead implantation tool. FIGS. 2A-3 show some exemplary implementations of tool-receiving elements. In FIG. 2A, the tool-receiving element is implemented as an aperture 248a suitable being removably received by a lead-receiving element, such as a protrusion, extending from a lead implantation tool. In FIG. 2B, the tool-receiving element is implemented as an eyelet 248b attached to the paddle body and suitable being removably received by a lead-receiving element, such as a protrusion, extending from a lead implantation tool. In FIG. 3, the tool-receiving element is implemented as a loop 348 of material (e.g., suture, or the like) suitable for being removably received by a lead-receiving element, such as a protrusion, extending from a lead implantation tool. Any of the above-described tool-receiving elements, and their like, are suitable for disposing/defining along either percutaneous or paddle leads.

The tool-receiving elements can be disposed at any suitable location along the lead. In at least some embodiments, the tool-receiving element is disposed along a distal portion of the lead. In at least some embodiments, the tool-receiving element is disposed at, or in proximity to, the distal-most portion of the paddle body (paddle lead) or lead body (percutaneous lead). In at least some embodiments, the tool-receiving element is disposed distal to each of the one or more electrodes. In at least some embodiments, the tool-receiving element is disposed distal to at least one of the one or more electrodes. In at least some embodiment, the paddle body includes multiple tool-receiving elements.

Figure 4A:
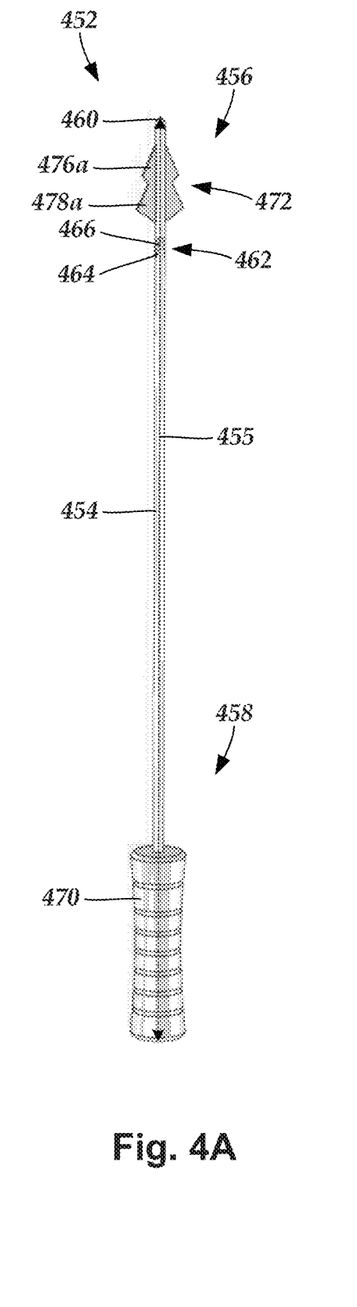
FIG. 4A is a first schematic perspective view of one embodiment of a lead implantation tool suitable for introducing an electrical stimulation lead into a patient, according to the invention.

Turning to FIG. 4A, stimulation leads are currently implantable in many different locations throughout a patient's body. Implantation of stimulation leads into some body locations suitable for receiving stimulation may be unduly challenging. For example, in the case of stimulation along regions of a patient's head external to their skull (e.g., occipital nerve, orbital nerve stimulation, or the like), a lead may be implanted along a patient's head and neck. The human head includes multifaceted geometries, typically with only a thin layer of tissue separating skin from bone. Additionally, the human head is a bodily region where it is desired to reduce as much potential cosmetic damage caused by a lead implantation procedure as possible. Accordingly, in some situations a medical practitioner may extend a lead from an incision made at a remote location along the patient's head to avoid making the incision along a portion of the patient's face. Unfortunately, introducing a lead along a tortuous path around a portion of a patient's skull within a thin layer of tissue may make conventional implantation techniques difficult.

Implantation of a paddle lead may be especially difficult due to the cross-sectional size of the paddle body along at least one dimension. In some instances, however, implantation of a paddle lead may be preferable to implantation of a percutaneous lead. In some instances, for example, although a paddle lead may be larger than a percutaneous lead along a width dimension, a paddle lead may be smaller than a percutaneous lead along a height dimension, which may promote a better fit in some confined spaces. Additionally, in some bodily locations, such as locations suitable for providing occipital nerve or orbital nerve stimulation, a paddle lead may be less prone to undesirable migration over time than a percutaneous lead. Moreover, a paddle lead may enable electrodes to be positioned or oriented such that the electrodes provide more favorable stimulation to the patient than is achievable with a percutaneous lead.

As herein described, a lead implantation tool can be used for: a) coupling with a stimulation lead; b) advancing along patient tissue with the stimulation lead coupled to the lead implantation tool; and c) separating from the stimulation lead while the lead is disposed in patient tissue. Once separated from the lead, the lead implantation tool can be removed from the patient leaving the stimulation lead within the patient. In at least some embodiments, the lead implantation tool separates from the stimulation lead as the lead implantation tool is removed from the patient. Paddle leads and percutaneous lead are described herein, for clarity of illustration. It will be understood that other types of leads (e.g., cuff leads, microstimulators) can be used in lieu of paddle leads or percutaneous leads.

In at least some embodiments, the lead implantation tool is suitable for separating patient tissue. In some embodiments, the lead implantation tool is suitable for separating enough patient tissue to form a tunnel of sufficient size and shape to receive a lead (e.g., a percutaneous lead, or a paddle lead). In other embodiments, the lead implantation tool is suitable for enlarging an existing tunnel to a size and shape sufficient to receive a lead (e.g., a percutaneous lead, or a paddle lead). Tunnel formation can occur either prior to advancement of the lead along patient tissue, or concurrently with advancement of the lead along patient tissue.

Figure 4B:
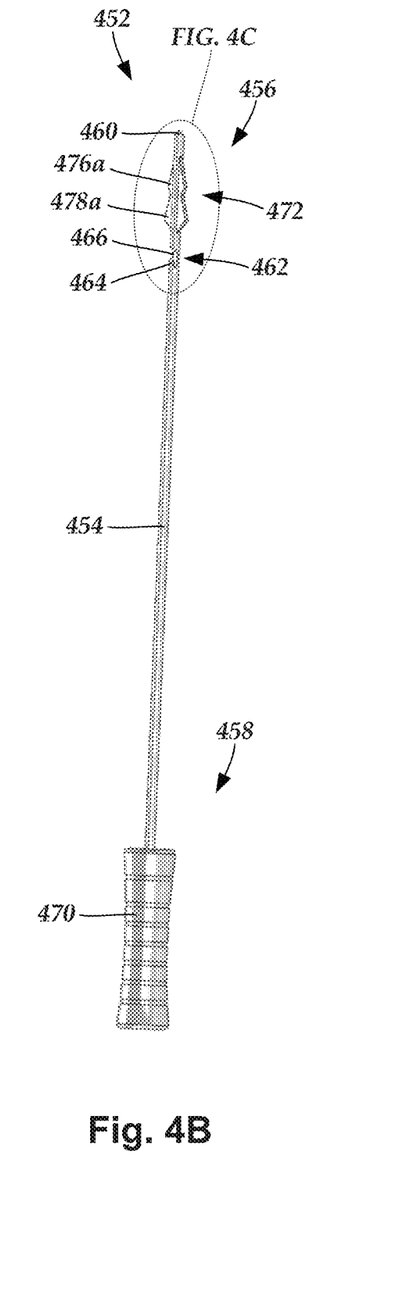
FIG. 4B is a second schematic perspective view of one embodiment of the lead implantation tool of FIG. 4A, according to the invention.
Figure 4C:
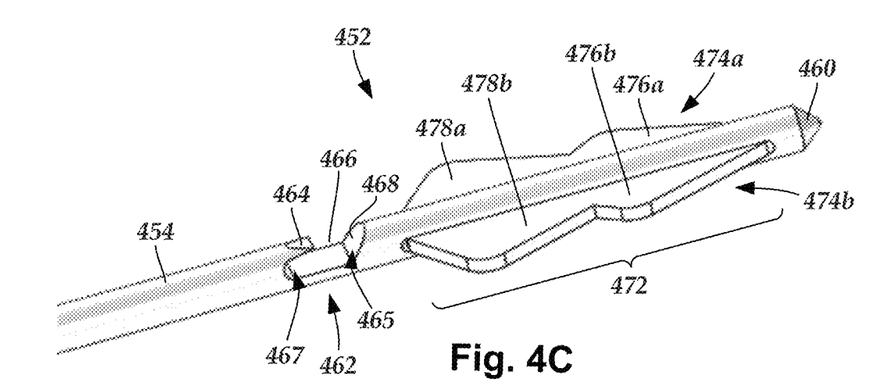
FIG. 4C is a schematic close-up, perspective view of one embodiment of a distal portion of the lead implantation tool of FIGS. 4A-4B, according to the invention.

FIG. 4A is a first schematic perspective view of one embodiment of a lead implantation tool 452 suitable for introducing an electrical stimulation lead (e.g., lead 212 of FIGS. 2A-2B; lead 312 of FIG. 3; or other leads) into a patient. The lead implantation tool 452 includes a body 454 having an elongated shape with a longitudinal length 455, a distal portion 456 and an opposing proximal portion 458. FIG. 4B is a second schematic perspective view of the lead implantation tool 452. FIG. 4C shows the distal portion of the body 454 of the lead implantation tool 452 in close-up, perspective view.

The body 454 can have any lateral profile (e.g., round, oval, capsule-shaped, or the like) suitable for introducing a lead and/or forming a tunnel. In FIGS. 4A-4C, the body is shown having a round lateral profile. Note that a lateral dimension is a dimension perpendicular to a longitudinal length of the body. Note also, that "lateral" and "transverse" may be used interchangeably herein.

The distal portion of the lead implantation tool is configured for insertion into a patient's body during a lead implantation procedure, while the proximal portion of the lead implantation tool is configured to remain external to the patient during a lead implantation procedure. In at least some embodiments, a handle 470 is disposed along the proximal portion of the body. The handle may facilitate a user's ability to control movement of the lead implantation tool while the distal portion of the lead implantation tool is inserted into a patient by improving the user's ability to grip the lead implantation tool.

The distal portion 456 of the body 454 includes a blunt tip 460 suitable for advancing the lead implantation tool 452 through patient tissue. In at least some embodiments, the blunt tip is suitable for separating patient tissue to form a tunnel within a patient. In at least some embodiments, the lead implantation tool does not pierce or core patient skin. In at least some embodiments, the bluntness of the tip renders the lead implantation tool insufficient to pierce patient skin. In at least some embodiments, an instrument with a sharpened tip (not shown) is used to form an entry for any tunnel formed or used by the lead implantation tool.

The body 454 is formed from any suitable biocompatible material(s) having sufficient column strength to extend along patient tissue. In some embodiments, the body 454 is formed from biocompatible material(s) having sufficient column strength to tunnel through patient tissue. In at least some embodiments, the body is formed from annealed steel. Other suitable materials can be used in lieu of, or in addition to, annealed steel including, for example, spring steel, surgical steel, or other metals, alloys, or other biocompatible non-metallic materials of suitable flexibility and strength for forming tunnels within patient tissue.

In at least some embodiments, the body is flexible. It may be advantageous for the body to be flexible enough to extend along different anatomical contours along which a tunnel is to extend, such as along a patient's head. In some embodiments, the body is flexible enough to bend at least 5°, 10°, 15°, 20°, 25°, 30°, 35°, 40°, 45°, 50°, 60°, 70°, 80°, 90°, or more along the length of the body during a lead introducing (or tunnel formation) procedure. In some embodiments, the body is flexible enough to bend at least 10° and no more than 80° during a lead introducing (or tunnel formation) procedure. In some embodiments, the body is flexible enough to bend at least 20° and no more than 60° during a lead introducing (or tunnel formation) procedure. In some embodiments, the body is flexible enough to bend at least 30° and no more than 50° during a lead introducing (or tunnel formation) procedure. In some embodiments, the lead implantation tool has sufficient flexibility to enable the lead implantation tool to bend around a portion (e.g., at least one-eighth, one-quarter, one-third, one-half, or more) of a circumference of a patient's skull.

A lead-receiving element 462 is disposed along the distal portion of the body. The lead-receiving element is configured to removably receive the lead. In at least some embodiments, the lead-receiving element is configured to receive the tool-receiving element of the lead (e.g., aperture 248a of FIG. 2A, eyelet 248b of FIG. 2B, loop 348 of FIG. 3, or the like). As described in more detail below, the lead-receiving element can be configured to retain the lead via, for example, the lead's tool-receiving element, while the lead implantation tool is advanced along patient tissue to target location; and to separate from the lead and be removed from the patient, leaving the lead behind in the patient.

The lead-receiving element can be implemented as any feature or apparatus that is coupled to, or coupleable to, or formed along the lead implantation tool and that is suitable for: a) coupling with and retaining a lead during advancement of the lead implantation tool along patient tissue; and b) separating (e.g., uncoupling, disengaging, detaching, dislodging, or the like) from the lead prior to, or during, removal (e.g., withdrawal, retraction, or the like) of the lead implantation tool from the patient.

In some embodiments, the lead-receiving element includes a protrusion 464 suitable for removably receiving one or more portions of the lead, such as the lead-receiving element. In some embodiments, the protrusion has a sharpened tip. In other embodiments, the protrusion has a rounded tip. In some embodiments, the protrusion is formed from a rigid material. In some embodiments, the protrusion is formed from the same material as the body of the lead implantation tool.

In some embodiments, the protrusion extends linearly from the body 454. In other embodiments, the protrusion includes at least one bend. In at least some embodiments, the protrusion extends parallel with a longitudinal length of the body. In some embodiments, the protrusion extends distally from the body. In at least some embodiments, the protrusion at least partially extends distally from the body. In at least some embodiments, the protrusion at least partially extends proximally from the body.

In at least some embodiments, the protrusion 464 is disposed in a cutout 466 that is defined along a side of the body. As best seen in FIG. 4C, the cutout has a distal end 465, a proximal end 467 and includes cutout surface walls 468. In FIG. 4C (and in other figures), the protrusion is shown jutting out from the cutout surface walls along the proximal end of the cutout and extending partially across the cutout towards the distal end of the cutout. In other embodiments, the protrusion extends from one or more other portions of the cutout surface walls in addition to, or in lieu of, the proximal end with at least a portion of the protrusion extending distally (towards the blunt tip). In some embodiments, the protrusion extends from the cutout surface walls along the distal end of the cutout and bends to form a hook-like (or J-like or U-like or C-like) shape at, or in proximity to, a distal end of the protrusion so that the distal end of the protrusion extends distally.

In at least some embodiments, the protrusion is entirely inset from, or flush with, an outer surface of the body. It may be advantageous for the protrusion to be entirely inset from, or flush with, the outer surface of the body to prevent the protrusion from damaging patient tissue when the lead implantation tool is advanced along patient tissue.

The cutout can extend into the body any suitable depth. Ranges of maximum depths may vary depending on different factors including, for example, one or more of the diameter of the body, the materials used to form the body, the types of tissue through which the lead implantation tool is extended, or other factors. It is advantageous for the cutout to provide sufficient depth to accommodate the protrusion and enable the protrusion to receive the lead with, optionally, a portion of the lead disposed in the cutout. However, it is also advantageous to maintain enough of the body along the cutout to prevent kinking or breakage of the lead implantation tool during a lead implantation (or tunnel formation) procedure. In at least some embodiments, the cutout extends into the body no more than two-thirds of the diameter of the body at the location of the cutout.

In some embodiments, the protrusion is formed from the body itself (i.e., a portion of the cutout is shaped to form the protrusion). In other embodiments, a protrusion-shaped feature is coupled to one or more portions of the cutout surface walls. Regardless of how the protrusion is formed, it may be advantageous for the protrusion to be flush with, or inset from, an outer surface of the body of the lead implantation tool to prevent the protrusion from potentially damaging patient tissue when the lead implantation tool is disposed in patient tissue and is moved relative to the tissue.

As mentioned above, the lead implantation tool can, optionally, be used to form the tunnel through which the lead is advanced during a lead implantation procedure. When the lead to be implanted is a percutaneous lead, the blunt tip can, in some embodiments, be used to separate enough tissue to form a tunnel of sufficient size to accommodate the lead implantation tool and the lead during implantation of the lead. When, however, the lead to be implanted is a paddle lead, the blunt tip by itself may not be sufficient for separating enough tissue to form a tunnel of adequate size to accommodate the paddle body.

In at least some embodiments, the lead implantation tool further includes one or more tissue-separating members 472. The one or more tissue separation members are configured to separate patient tissue to expand a tunnel formed by the blunt tip along at least one lateral dimension while the body is advanced along patient tissue. The tunnel formed by the lead implantation tool with tissue-separating members is larger along at least one lateral dimension than a tunnel formed by embodiments of the lead implantation tool without tissue-separating members. In at least some embodiments, the tissue-separating members are configured for forming a tunnel of sufficient size and shape to enable a paddle body of a paddle lead to be advanced along the tunnel.

The tissue separation members are formed as one or more blades extending radially outward from the distal portion of the body of the lead implantation tool. In at least some embodiments, the interface between the one or more blades and the body of the lead implantation tool extends longitudinally along the body. In at least some embodiments, the blades are blunt. In at least some embodiments, the blades are configured for neither piercing nor coring patient skin during a lead implantation (or tunnel formation) procedure.

In some embodiments, the blades are formed as single-peaked structures. In other embodiments, the tissue separation members are formed as multi-peak structures with multiple peaks that are longitudinally-offset from, and radially-aligned with, one another. As best shown in FIG. 4C, the illustrated embodiments show multi-peak structures 474*a*, 474*b* with first peaks 476*a*, 476*b*, respectively, and second peaks 478*a*, 478*b*, respectively. The second peak(s) extend radially outward from the body by a larger amount than their respective first peaks and can be used to further expand the transverse length of the tunnel from the size of the tunnel formed by the first peak. Alternatively, instead of implementing a multi-peak structure, the same, or similar, effect can be achieved by longitudinally aligning multiple single-peak structures along the body, where more proximally disposed single-peak structures extend radially outward from the body by larger amounts than the more distally disposed single-peak structures.

In at least some embodiments, the lead implantation tool includes two tissue-separating members circumferentially offset from one another along the body 454 by 180 degrees (as shown in FIGS. 4A-4C). In embodiments with multiple tissue-separating members, the tissue-separating members can be longitudinally even with one another, or longitudinally staggered from one another along the longitudinal length of the body. In the illustrated embodiments, the two tissue-separating members are shown being longitudinally even with one another along the longitudinal length of the body.

The lead-receiving element can be proximal to, distal to, or overlap with, at least one tissue separation member along the longitudinal length of the body. In the illustrated embodiments, the lead-receiving element is shown proximal to each of two tissue separation members along the longitudinal length of the body. In at least some embodiments, a distal-most portion of the protrusion is no more than 1 inch (2.5 cm), 0.9 inches (2.3 cm), 0.8 inches (2 cm), 0.7 inches (1.8 cm), 0.6 inches (1.5 cm), 0.5 inches (1.3 cm), 0.4 inches (1 cm), 0.3 inches (0.8 cm), from the blunt tip 460 of the lead implantation tool.

Figure 5A:
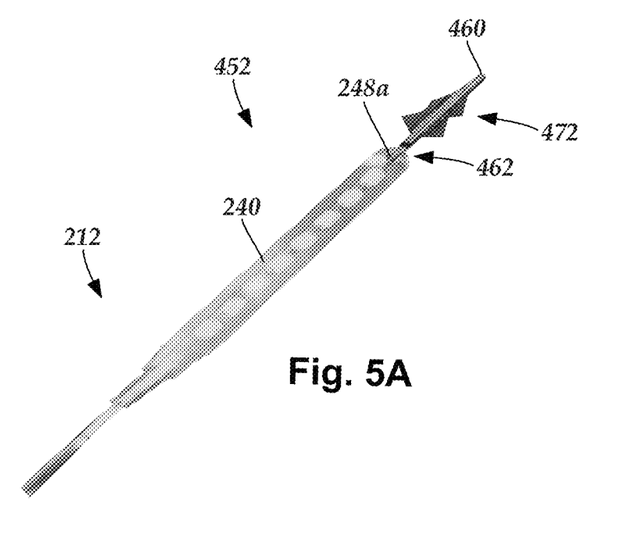
FIG. 5A is a first side view of one embodiment of the paddle lead of FIG. 2A coupled to the lead implantation tool of FIGS. 4A-4C, according to the invention.
Figure 5B:
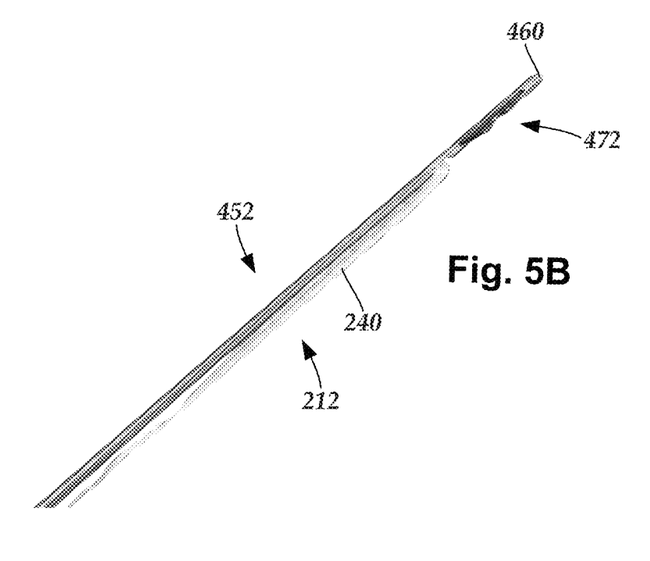
FIG. 5B is a second side view of one embodiment of the paddle lead of FIG. 2A coupled to the lead implantation tool of FIGS. 4A-4C, according to the invention.
Figure 5C:
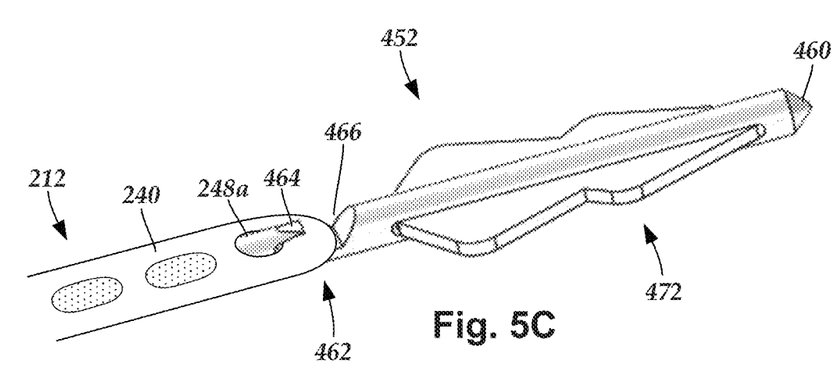
FIG. 5C is a schematic close-up, perspective view of one embodiment of a distal portion of the paddle lead of FIG. 2A coupled to the lead implantation tool of FIGS. 4A-4C, according to the invention.

Turning to FIGS. 5A-5C, a lead is removably coupled to the lead implantation tool prior to advancement of the lead into a patient. FIG. 5A shows, in a first side view, one embodiment of the paddle lead 212 coupled to the lead implantation tool 452. FIG. 5B shows the paddle lead 212 coupled to the lead implantation tool 452 from a second side view. In at least some embodiments, the lead is coupled to the lead implantation tool solely by a single coupling between the tool-receiving element of the lead and the lead-receiving element of the lead implantation tool. In other embodiments, the lead is coupled to the lead implantation tool via multiple couplings.

In embodiments of the lead implantation tool with tissue-separation members circumferentially offset by 180 degrees, such as the embodiment shown in FIGS. 5A-5C, the lead-receiving element can be circumferentially offset from each of the two tissue separation members by any suitable amount, including being circumferentially even with one or more of the tissue separation members. With regards to paddle leads, in some embodiments the lead-receiving element is circumferentially offset from the one or more tissue separation members by an amount sufficient to align the width dimension of the paddle body with the direction that at least one of the one or more tissue separation members extend outwardly from the body of the lead implantation tool when the lead is coupled to the lead implantation tool.

As shown in FIGS. 5A-5C (and in other figures), the lead-receiving element 462 is circumferentially offset from each of the two tissue separation members 472 by 90 degrees so that the width of the paddle body is parallel with the direction that the directions that the tissue separation members extend outwardly from the body of the lead implantation tool when the lead is coupled to the lead implantation tool. In some embodiments, the lead-receiving element 462 is circumferentially offset from each of the two tissue separation members 472 by approximately 90 degrees. In some embodiments, the lead-receiving element 462 is circumferentially offset from each of the two tissue separation members 472 by no less than 70 degrees and no more than 110. In some embodiments, the lead-receiving element 462 is circumferentially offset from each of the two tissue separation members 472 by no less than 80 degrees and no more than 100.

In at least some embodiments, the lead implantation tool 452 is isodiametric along the entire longitudinal length of the body proximal to the blunt tip. In at least some embodiments, the lead-implantation tool 452 is isodiametric along the entire longitudinal length of the body proximal from the blunt tip 460 and distal to the handle (470 in FIGS. 4A-4B). In at least some embodiments, the lead implantation tool 452 is isodiametric along the entire longitudinal length of the portion of the body insertable into a patient proximal from the lead-receiving element. In at least some embodiments, the lead implantation tool 452 is isodiametric along the entire longitudinal length of the portion of the body insertable into a patient proximal from the proximal-most tissue-separating member.

FIG. 5C shows, in close-up, perspective view, one embodiment of a distal portion of the paddle body 240 of the paddle lead 212 (as shown in FIG. 2A) coupled to a distal portion of the body 454 of the lead implantation tool 452. As shown in FIG. 5C, the protrusion 464 of the lead-receiving element 462 is extended through the aperture 248a defined in the paddle body 240. The cutout 466 is shown having sufficient size and depth to accommodate a portion of the lead within the cutout. The lead-receiving element is configured to retain the paddle body 240 as the lead implantation tool 452 is moved forwardly (advanced), and to separate from the paddle body 240 when the lead implantation tool 452 is moved rearwardly (retracted, withdrawn).

Figure 6:
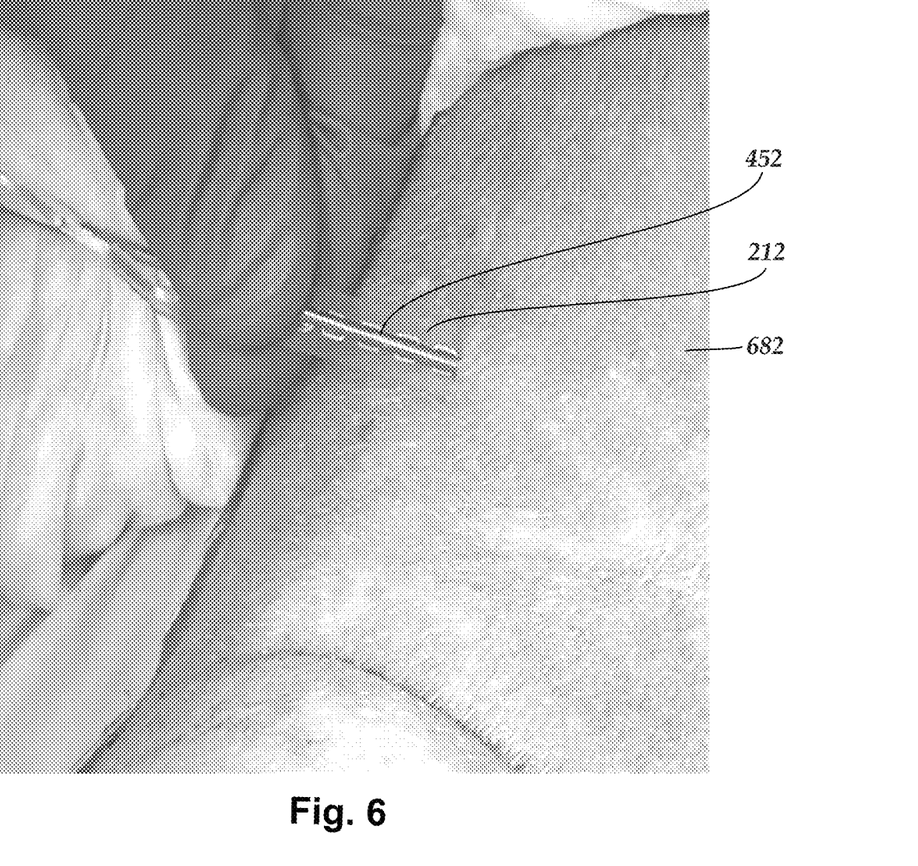
FIG. 6 is a schematic view of one embodiment of the paddle lead of FIG. 2A being introduced into a patient using the lead implantation tool of FIGS. 4A-4C, according to the invention.

Turning to FIG. 6, in at least some embodiments when a lead is coupled to the lead implantation tool the lead can be advanced within patient tissue to a desired location, such as a target stimulation location, and separated from the lead implantation tool. The lead implantation tool can be removed from the patient leaving the lead at, or in proximity to, the separation location. The proximal end of the lead can be coupled to a control module and, if applicable, the control module can be implanted using conventional techniques.

The lead implantation tool can, optionally, be used to form the tunnel through which the lead implantation tool guides the lead. In some embodiments, the lead implantation tool is used to form the tunnel prior to being used to advance the lead along the tunnel. In other embodiments, the lead implantation tool is used to concurrently form the tunnel and advance the lead along the tunnel.

FIG. 6 shows, in schematic view, one embodiment of the paddle lead 212 being introduced into a patient 682 using the lead implantation tool 452. In FIG. 6, the paddle lead is being introduced into a posterior portion of the patient's head. The lead is angled to advance the lead around a portion of the circumference of the patient's head while remaining external to the patient's skull.

An exemplary technique for implanting a stimulation lead into a patient includes coupling the lead-retention element of the lead implantation tool to a distal portion of a stimulation lead, such as the tool-receiving element. In some embodiments, the lead-retention element of the lead implantation tool is coupled to the tool-receiving element of the lead. In some embodiments, a protrusion of the lead-receiving element is extended through an aperture, loop, eyelet, or the like of the tool-receiving element of the lead.

The lead implantation tool is advanced through a tunnel formed in patient tissue with the distal portion of the electrical stimulation lead coupled to the lead-retention element. The lead-retention element is separated from the stimulation lead at a desired location (e.g., a target stimulation location) along the tunnel. Note that, in embodiments where the lead-receiving element is proximal to the tip of the lead implantation tool, the tip of the lead implantation tool may be extended beyond the desired separation location so that the lead-receiving element aligns with the desired separation location when the lead is separated from the lead implantation tool.

The lead implantation tool is then retracted (withdrawn, removed) along the tunnel leaving the stimulation lead within the patient. In some embodiments, the lead is separated from the lead implantation tool solely by reversing direction of the lead implantation tool (i.e., retracting/withdrawing/removing the lead implantation tool along the tunnel). In other embodiments, the lead is separated from the lead implantation tool as a result of one or more specific movements of the lead implantation tool, such as one or more twists, prior to retraction of the lead implantation tool. In some embodiments, the specific movements may be correlated to the shape of the protrusion.

The lead implantation tool is, optionally, used to form the tunnel. Tunnel formation can be performed prior to, or concurrently with, advancement of the lead along patient tissue. Tunnel formation can be performed with, or without, the lead being coupled to the lead implantation tool. The tunnel can be formed to accommodate different types of leads. For example, the tunnel can be formed to accommodate a paddle lead or a percutaneous lead. In some embodiments, the tunnel is formed without the lead coupled to the lead implantation tool, then the tunnel is subsequently expanded, either with or without the lead being coupled to the lead implantation tool.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A lead implantation tool for facilitating implantation of a stimulation lead into a patient, the lead implantation tool comprising:
   a body having an elongated shape with an outer surface, a longitudinal length, a diameter, a proximal portion, and a distal portion with a blunt tip configured and arranged to separate patient tissue to form, or extend through, a tunnel in the patient tissue when the body is advanced along the patient tissue; and
   a lead-retention element formed along the distal portion of the body, the lead-retention element comprising
      a cutout defined along a side of the body and comprising a cutout surface wall inset from the outer surface of the body, and a portion of the body defining a protrusion extending outwardly from above a portion of the cutout surface wall over a portion of the cutout and extending towards the blunt tip, wherein at least a portion of the protrusion, directly contiguous with a remainder of the body proximal of the cutout, is flush with the outer surface of the remainder of the body proximal of the cutout, the protrusion configured and arranged to removably receive and retain a portion of the stimulation lead while the distal portion of the body is advanced along the patient tissue and to separate from the stimulation lead as the distal portion of the body is withdrawn from the tunnel in the patient tissue.

2. The lead implantation tool of claim 1, further comprising one or more tissue separation members extending radially outward from the outer surface of the distal portion of the body, the one or more tissue separation members configured and arranged to separate patient tissue to expand the tunnel along at least one lateral dimension when the body is advanced along patient tissue.

3. The lead implantation tool of claim 2, wherein each of the one or more tissue separation members comprises a multi-peak structure with a first peak and at least one second peak that is longitudinally-offset from and radially-aligned with the first peak along the body of the lead implantation tool.

4. The lead implantation tool of claim 2, wherein the protrusion is proximal to an entirety of each of the one or more tissue separation members along the longitudinal length of the body.

5. The lead implantation tool of claim 2, wherein the lead implantation tool comprises two of the tissue separation members which are circumferentially offset from one another along the body by 180 degrees.

6. The lead implantation tool of claim 5, wherein the protrusion is circumferentially offset from each of the two tissue separation members along the body by at least 70 degrees and no more than 110 degrees.

7. The lead implantation tool of claim 1, wherein a distal-most portion of the protrusion is longitudinally-offset from the blunt tip by no more than 2 cm.

8. The lead implantation tool of claim 1, wherein the protrusion extends parallel to the longitudinal length of the body.

9. The lead implantation tool of claim 1, wherein the body is flexible.

10. The lead implantation tool of claim 1, further comprising a handle disposed along the proximal portion of the body.

11. A medical device kit, comprising:
the lead implantation tool of claim 1; and
a stimulation lead comprising
a lead body having an elongated shape with a proximal portion and a distal portion, and
a tool-receiving element configured and arranged to removably couple with the lead-retention element of the lead implantation tool so that, when the tool-receiving element is coupled with the lead-retention element, movement of the lead implantation tool causes a corresponding movement of the distal portion of the lead body of the stimulation lead.

12. The medical device kit of claim 11, wherein the tool-receiving element is formed as one of an aperture, an eyelet, or a loop of material.

13. The medical device kit of claim 11, wherein the stimulation lead is an electrical stimulation lead, the electrical stimulation lead comprising at least one terminal disposed along the proximal portion of the lead body and at least one electrode coupled to the at least one terminal.

14. The medical device kit of claim 13, wherein the electrical stimulation lead is a paddle lead with a paddle body disposed along the distal portion of the lead body, and wherein the at least one electrode is disposed along the paddle body.

15. The medical device kit of claim 14, wherein the tool-receiving element is disposed along the paddle body.

16. A method for implanting a stimulation lead into a patient, the method comprising:
providing the lead implantation tool of claim 1;
coupling the lead-retention element of the lead implantation tool to a distal portion of the stimulation lead;
advancing the lead implantation tool along a tunnel formed along patient tissue with the distal portion of the stimulation lead coupled to the lead-retention element;
separating the lead-retention element from the stimulation lead; and
removing the lead implantation tool from the tunnel leaving the stimulation lead disposed in patient tissue.

17. The method of claim 16, wherein separating the lead-retention element from the stimulation lead comprises withdrawing the lead implantation tool along the tunnel, the withdrawal causing the stimulation lead to separate from the protrusion of the lead-retention element.

18. A method for implanting a stimulation lead into a patient, the method comprising:
providing the lead implantation tool of claim 1;
forming a tunnel in patient tissue using the lead implantation tool;
coupling the lead-retention element of the lead implantation tool to a distal portion of the stimulation lead;
advancing the lead implantation tool through the tunnel with the distal portion of the stimulation lead coupled to the lead-retention element;
separating the lead-retention element from the stimulation lead; and
removing the lead implantation tool from the tunnel leaving the stimulation lead within the patient.

19. The method of claim 18, wherein forming a tunnel in patient tissue using the lead implantation tool comprises forming a tunnel configured and arranged to receive a paddle body of the stimulation lead.

20. A method for implanting a stimulation lead into a patient, the method comprising:
providing the lead implantation tool of claim 1;
coupling the lead-retention element of the lead implantation tool to a distal portion of the stimulation lead;
advancing the lead implantation tool along patient tissue with the distal portion of the stimulation lead coupled to the lead-retention element; and
separating the lead-retention element from the stimulation lead as the lead implantation tool is withdrawn from the patient tissue.

* * * * *